United States Patent
Mawad

(10) Patent No.: US 6,746,393 B2
(45) Date of Patent: *Jun. 8, 2004

(54) RETRIEVABLE, SHIELDED RADIOTHERAPY IMPLANT

(75) Inventor: Michel E. Mawad, Houston, TX (US)

(73) Assignee: MRKR L.L.C., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/208,356

(22) Filed: Jul. 30, 2002

(65) Prior Publication Data

US 2002/0193654 A1 Dec. 19, 2002

Related U.S. Application Data

(63) Continuation of application No. 09/526,322, filed on Mar. 15, 2000, now Pat. No. 6,428,462, which is a continuation of application No. 08/615,566, filed on Mar. 11, 1996, now Pat. No. 6,056,686, which is a continuation of application No. 08/122,199, filed on Sep. 15, 1993, now Pat. No. 5,498,227.

(51) Int. Cl.[7] .................................. A61N 5/00
(52) U.S. Cl. ............................................ 600/3
(58) Field of Search ......................... 600/1–8

(56) References Cited

U.S. PATENT DOCUMENTS 5,498,227 A * 3/1996 Mawad ..................... 600/3

* cited by examiner

Primary Examiner—John P. Lacyk
(74) Attorney, Agent, or Firm—Conley Rose, P.C.

(57) ABSTRACT

A radiotherapy device comprises a radioactive wire adapted to deliver an intended dosage of radiation to a lesion or other selected body tissues. The radioactive wire comprises an inner core about which is disposed an outer buffer layer of platinum or other suitable metal of high atomic number. The buffer layer preferably comprises a thin, continuous wire wrapped about the inner core. The radiotherapy device may be made into a variety of shapes, such as a straight wire, a helical coil, or other more complex shape, and it may be provided with an elastic memory. The device may be adapted for attachment to a delivery wire for controlled placement, as through a delivery catheter or microcatheter, at the treatment site. When accurate positioning of the device is not necessary, it can simply be injected through the delivery catheter or microcatheter, and in that event a delivery wire is not needed. The device may be provided with mechanically or electrically releasable means for attachment to the delivery wire during delivery, and for releasing the device at the treatment site. The device may be provided with a shoulder, hook, or other suitable gripping means on its distal end, which can be lassoed by a micro-snare device for retrieving the device from the body.

4 Claims, 2 Drawing Sheets

RETRIEVABLE, SHIELDED RADIOTHERAPY IMPLANT

This is a continuation of application Ser. No. 09/526,322, filed Mar. 15, 2000, now U.S. Pat. No. 6,428,462, which is a continuation Ser. No. 08/615,566, filed Mar. 11, 1996 now U.S. Pat. No. 6,056,686; which is a continuation of application Ser. No. 08/122,199 filed Sep. 15, 1993, now U.S. Pat. No. 5,498,227.

BACKGROUND OF THE INVENTION

The present invention relates to the field of radiotherapy devices, and more particularly to the field of implantable, permanent or retrievable radiotherapy devices. More particularly still, the present invention relates to the field of shielded radioactive wires adapted for implantation at the site of a lesion or other selected body tissue for treatment of cancer or other pathological condition.

At present, external beam radiotherapy is widely utilized in the treatment of cancer and more recently, in the treatment of vascular malformations particularly those affecting the Central Nervous System. Radiotherapy is used as an adjunct to surgical excision and chemotherapy, or as the sole form of treatment.

External beam radiotherapy can be either nonfocused or stereotactic using a gamma knife apparatus or a linear accelerator. Both of these radiotherapy modalities are limited by the undesirable side effect of radiation necrosis they produce in the normal tissue surrounding the lesion to be irradiated.

Interstitial brachytherapy is a form of therapy which delivers local radiation to a lesion using permanent implants (seeds) which are surgically inserted in or very close to the area of interest. Theoretically, brachytherapy allows the delivery of a high dose of radiation to the abnormal or cancerous tissue with minimal or limited damage to the adjacent normal structures. Interstitial brachytherapy is often utilized to supplement surgical excision of a tumor or in combination with external beam radiotherapy. The permanent implants used in interstitial brachytherapy are inserted in the tumor bed during direct surgical exposure or utilizing a stereotactic localization device.

It would be desirable to provide a brachytherapy device that can be inserted percutaneously in cancerous lesions or vascular malformations through a microcatheter introduced in the body via the arterial tree, the venous system, or any other physiologic collecting or drainage ductal system. This would provide a relatively simple, cost effective, and medically effective treatment which would also be relatively easy to implant in the patient's body. Using a procedure of this type would in most cases be less traumatic to the tissues involved, and would thus be less risky than traditional methods of interstitial brachytherapy. In addition, it would be desirable to provide such a brachytherapy device that can be retrieved and replaced if necessary or desired, or left permanently in place.

Presently, there are several types of embolic devices available which can be introduced in the arterial or the venous system through a microcatheter. One such device is in the form of a thin metallic coil or a thin composite metallic wire that can be preloaded in a polyethylene sheath and introduced percutaneously into the area of interest through the microcatheter. This known device can be delivered using a controlled delivery mechanism or simply injected through the catheter.

The embolic devices referred to in the previous paragraph are currently used for their thrombogenic effect to occlude blood vessels. It would be advantageous to use such known systems not only for such purposes, but also for the dual purpose of an implantable radiation device. This way, the simple, effective delivery systems now known for thrombogenic treatments can also serve as radiotherapy delivery systems.

SUMMARY OF THE INVENTION

The radiotherapy device of the present invention comprises a wire of radioactive material which is designed and adapted to deliver an intended dosage of radiation to a lesion or other selected body tissues. The wire of radioactive material preferably comprises an inner core about which is disposed an outer buffer layer of platinum or other suitable metal of high atomic number. The outer buffer layer may comprise a relatively thin, continuous wire of round, flat, or other suitable cross-section, wrapped in spiral or helical fashion about the inner core, and is adapted to attenuate the radiation. The radiotherapy device of the present invention may be made into a variety of shapes or configurations depending, for example, on the anatomy of the vessel or ductal system or other body tissue where the device will be inserted or used. For example, the device may be shaped into a straight wire, or it may be formed into a helical coil or coils or other more complex shape. The device may be provided with an elastic memory whereby it has a helical or other desired shape in the relaxed state, but may be inserted into the tissue, vessel, or the like in a straightened configuration; and then when released or inserted into the treatment site, it may resume or regain its original, relaxed (e.g., helical) shape.

The radiotherapy device of the present invention may be adapted for attachment to a delivery wire for controlled placement, as through a catheter or microcatheter disposed over a guide wire, at the intended treatment site. The delivery wire and the radiotherapy device of the present invention are preferably sufficiently radiopaque so as to enable easy fluoroscopic visualization in the insertion or delivery process. When accurate positioning of the radiotherapy device of the present invention is not necessary, it can simply be injected through the delivery catheter or microcatheter. In the latter event, a delivery wire is not needed.

The radiotherapy device of the present invention may be provided with mechanically or electrically releasable means for attaching the device to the delivery wire during the delivery process, and for releasing the device at the treatment site to allow removal of the delivery catheter and guide wire, thus leaving the radiotherapy device present at the treatment site either permanently or for later retrieval. With regard to electrically releasable attachment means, a soldered connection between the delivery wire and the radiotherapy device of the present invention may be released through electrolysis by application of a small direct current to the joint. A mechanically releasable attachment means for the radiotherapy device of the present invention may comprise a pair of interengaging hooks disposed, respectively, on the distal end of the delivery wire and the proximal end of the radiotherapy device.

The radiotherapy device of the present invention may be used as a permanent implant, or alternatively, it can be adapted to permit retrieval and replacement. A retrievable embodiment of the radiotherapy device of the present invention includes a head having a shoulder, hook, or the like on its distal end which may be lassoed by a microsnare device, again delivered through a microcatheter or the like, and easily pulled from the body through the same microcatheter.

These and other objects and advantages of the invention will become apparent from the following description of the preferred embodiment when read in conjunction with reference to the following drawings, wherein:

DESCRIPTION OF THE PREFERRED EMBODIMENT

Figure 1:
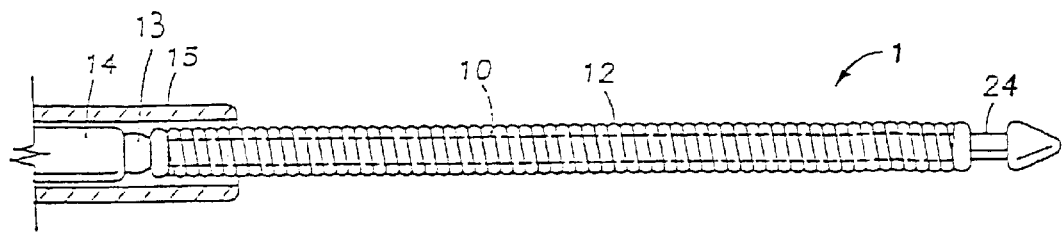
FIG. 1 is a view, partly in elevation and partly in vertical section, of one embodiment of a retrievable radiotherapy device of the present invention attached by solder to the distal end of a delivery wire and extending from the distal end of a delivery catheter.

Referring to FIG. 1, the device 1 of the present invention preferably comprises a wire 10 of radioactive material which is designed and adapted to deliver the intended dosage of radiation to the lesion or other selected body tissues. The dosage of radiation to be delivered by the device, both in terms of the total amount of radiation delivered to the site over the useful life of the device 1 and its rate, is selected to be consistent with the plan of radiotherapy treatment of the lesions or other tissues, which may of course be in conjunction with other treatment modalities, such as excision or chemotherapy. Any of a variety of radioisotopes can be used in the present device, for example, cobalt-60, cesium-137, iridium-192, iodine-125, palladium-103, tantalum-73, tungsten-74, or gold-198. The wire 10 may be rendered radioactive by, for example, incubation in an accelerator for several hours prior to its implantation in the body. Typically, incubation for anywhere between about 24 and 48 hours will be required to ensure the proper radioactivity of the wire 10. It will be appreciated that the dose of radioactivity to be delivered by the device and its hourly emission rate can be customized to suit the need of the radiation oncologist or other health professional, and the therapeutic requirement of the lesion or other tissue requiring treatment. The dose will typically be proportional to the period of incubation of the device in the accelerator and/or to the physical length and thickness of the wire 10. Inner core 10 preferably has a diameter of about ten thousandths of an inch to about fifty thousandths of an inch (about 0.010" to 0.050"). Inner core 10 preferably has a length of about 1 millimeter to about 40 centimeters (about 1 mm to 40 cm). Of course, the diameter and length of wire 10 can vary depending on the size of the delivery system, if any, to be used in placing the device in the body, the size or location of the vessel or other body tissue in or through which it will be implanted, the intended radioactivity of the device, or other factors such as the ease of handling or of manipulating the device.

Wire 10 preferably comprises an inner core for the present device about which is disposed an outer buffer layer 12 of platinum or other suitable metal of high atomic number. The outer buffer layer 12 is adapted to attenuate the radiation. The outer buffer layer 12 preferably may comprise a relatively thin, continuous wire of round, flat, or other suitable cross-section, wrapped in spiral or helical fashion about the inner core 10. The diameter of the buffer wire 12 preferably may be about ten thousandths of an inch to about fifty thousandths of an inch (about 0.010" to 0.050").

The device comprising the inner core 10 wrapped by outer buffer layer 12 may be made into a variety of shapes or configurations depending, for example, on the anatomy of the vessel or ductal system or other body tissue where the device will be inserted or used. For example, the device may be shaped into a straight wire, or it may be formed into a helical coil or coils or other more complex shape. If a helical coil is desired, the coil may vary in length and diameter of the helix, again depending on factors such as those referred to above. If a helical coil is used, it may be provided with a helical memory whereby the device may be inserted into the tissue, vessel, or the like in a straightened configuration, and then when released or inserted into the treatment site, the coil may resume or regain its helical shape. The outside diameter of the helix may vary from about 1 millimeter to about 2 centimeters, for example.

Figure 3:
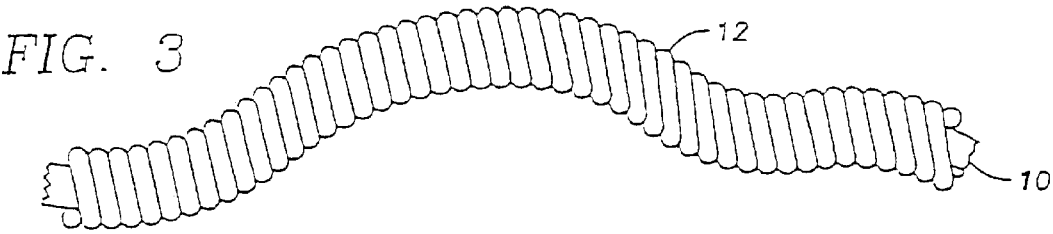
FIG. 3 is a fragmentary elevational view of an embodiment of a flexible radiotherapy device of the present invention, in a randomly assumed, undulating configuration.

The device 1 of the present invention may also be flexible enough to take on any random shape in its relaxed state (i.e., after being inserted into or released at the intended treatment site), such as the undulating configuration illustrated in FIG. 3.

Figure 5:
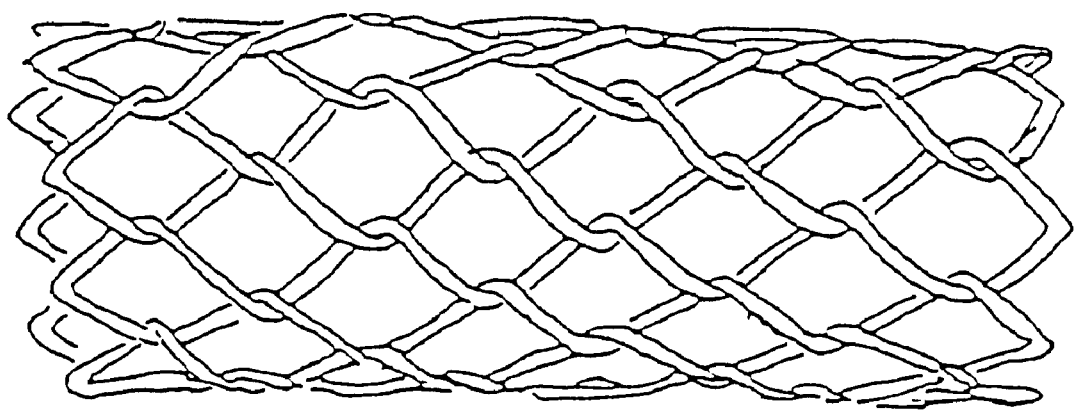
FIG. 5 is a side elevation of an alternative empodiment of a radiotherapy device in accordance with the present invention.

If desired, the device 1 of the present invention may even be used as a radioactive, expandable stent. For this purpose, one embodiment of such a device may comprise a radioactive wire 10 preformed into a helical coil, i.e. a "coil spring" shaped device, which has an elastic memory and a central, longitudinal axial passageway. The device may be inserted into a vessel, duct, or the like in a relatively straightened or reduced diameter state, as through a catheter or microcatheter or the like. When released at the treatment site, the helical memory may cause the helix to expand, either to its full, relaxed state diameter or to an expanded but restricted diameter. In another embodiment of such a device, as shown in FIG. 5, the radioactive wire 10 may be preformed into a wire mesh-like material, somewhat like miniature "chicken wire," and rolled into a cylindrical shape, again with a central, longitudinal axial passageway. This embodiment of the radioactive stent of the present invention can be fixed into such a hollow cylindrical shape as by mini-spot welding or other suitable means. A radioactive stent such as this latter type could be preloaded, in a smaller diameter, onto a deflated balloon device. Then, when the balloon is in place at the desired location, along with the radioactive, wire mesh expandable stent, the balloon is inflated to the desired diameter (such as the inside diameter of the duct), and this also expands the stent diameter. When the balloon is deflated and retrieved, the expanded radioactive stent is left in place in the duct. Such radioactive, expandable stents as referred to above may be used to deliver the intended radiation as well as to maintain the patency of, for example, a partially occluded, stenotic or strictured duct, vessel, or draining system of the patient's body. It will be appreciated that the diameter and length of the radioactive stent of the present invention can be selected as desired, or customized, to fit the anatomy of the lesion or other tissue site at which the stent will be used.

The device 1 of the present invention may be attached to a stainless steel or other suitable wire 14 or the like for use in delivering the device to the intended body tissue site. If a delivery catheter, or microcatheter, is to be used for inserting the device 1 into the desired body tissue site, it will be appreciated that the size of the stainless steel or other suitable wire 14 is selected so that it will fit into the inner diameter of the delivery catheter, such as that shown at 15, if used. Typically, the delivery catheter, which is known in the art, will be inserted into the artery, vein, duct, or other tissue with the aid of a guide wire or the like. Fluoroscopy is usually used to visualize the operation, so that the guide wire and delivery catheter are properly positioned. When the delivery catheter is so positioned, fluoroscopy may again be used when the device 1 is inserted through the delivery catheter to ensure that the device is properly located in the lesion or other body tissue. The stainless steel wire 14 and the composite metal device 1 are preferably sufficiently radiopaque so as to enable easy fluoroscopic visualization in the insertion or delivery process.

If desired, the device 1 of the present invention may be provided with mechanically or electrically releasable means for attaching the device to the delivery wire during the delivery process, and for releasing the device at the treatment site to allow removal of the delivery catheter and guide wire, thus leaving the device 1 present at the treatment site either permanently or for later retrieval, again if desired. Both electrically releasable and mechanically releasable attachment means are known in the art, for example, for attaching a thrombogenic platinum coil or the like to a stainless steel delivery wire. For example, Guglielmi has developed an electrically releasable attachment between a small platinum wire coil and a stainless steel delivery wire whereby the junction between the coil and delivery wire is soldered. An electrode, more particularly an anode, is attached to the delivery wire, and another electrode, and more particularly a ground or cathode, is attached to the body at, for example, a remote site. The electrodes are then attached to a current generator, such as a battery-operated unit, and a low positive d.c. current is applied to the delivery wire. This causes the solder or the stainless steel wire at the junction, which is typically left uninsulated, to dissolve by electrolysis and thus to release the device 1 at the treatment site. Electrolysis will typically cause the metal to dissolve and release the device 1 within about 12 to 15 minutes. A soldered joint, for example, between the delivery wire 14 and the inner core 10 and/or the outer buffer layer 12 of the radiotherapy device 1 of the present invention is shown at 13 in FIG. 1.

Figure 2:
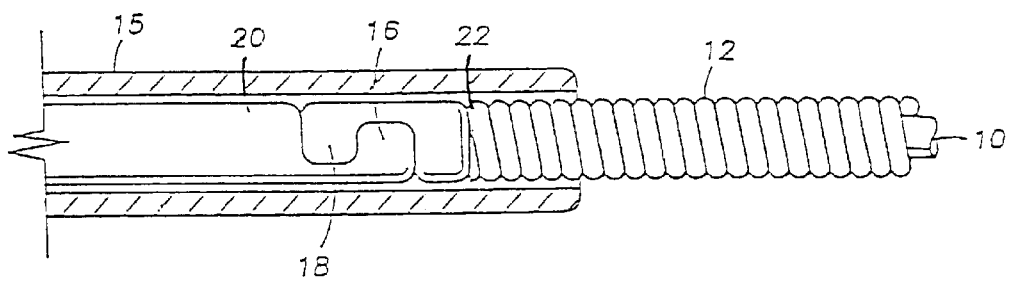
FIG. 2 is a fragmentary view, partly in elevation and partly in vertical section, of an alternative embodiment of a radiotherapy device of the present invention attached by interengaging hooks to the distal end of a delivery wire and extending from the distal end of a delivery catheter.

Alternatively, a releasable attachment for the present invention may comprise a pair of interengaging hooks 16, 18 disposed, respectively, on the distal end 20 of the delivery wire 14 and the proximal end 22 of the radiotherapy device 1 of the present invention. One example of such an arrangement is shown, for example, in FIG. 2. The hooks 16, 18 may be made in a variety of shapes, such as U- or J-shaped, barb-shaped, or the like, so long as they remain in a relatively snugly interfitted state during the delivery process and are restrained from becoming separated by the walls of the delivery catheter. One such arrangement of mechanical attachment means has been developed by Marks. When a device 1 which is provided with such mechanical attachment means as hooks 16, 18 is caused to exit from the distal end of the delivery catheter 15, the walls of the delivery catheter no longer restrain the hooks from becoming separated, thus allowing the hooks to disengage from one another and to free the radiation device 1 at the intended treatment site.

When accurate positioning of the device 1 is not necessary, it can simply be injected through the delivery catheter or microcatheter 15. Radiotherapy devices 1 of the present invention designed to be simply injected through the delivery catheter or microcatheter 15 need not be attached to any delivery wire 14. Where more accurate positioning of the device 1 is necessary or desired, a controlled delivery system or a simple pusher can be used. Controlled delivery can be accomplished either with the electrically releasable attachment means or the mechanically releasable attachment means referred to above. The term controlled delivery is intended to mean that the device 1 will be more accurately and precisely placed in the selected body tissues, as and when desired. Thus, with either the electrical or the mechanical release methods referred to above, the device 1 is first accurately and precisely placed in the desired tissue, usually with the aid of fluoroscopy. Then, either the current is applied to the delivery wire to dissolve by electrolysis the metal at the uninsulated portion of the wire (e.g., at the junction between the device 1 and the delivery wire 14) and thereby to release the device, or the delivery wire is pushed longitudinally axially to push the device 1 from the distal end of the catheter or microcatheter 15, thereby allowing the disengagement of the hooks 16, 18 and release of the device in this fashion.

Figure 4:
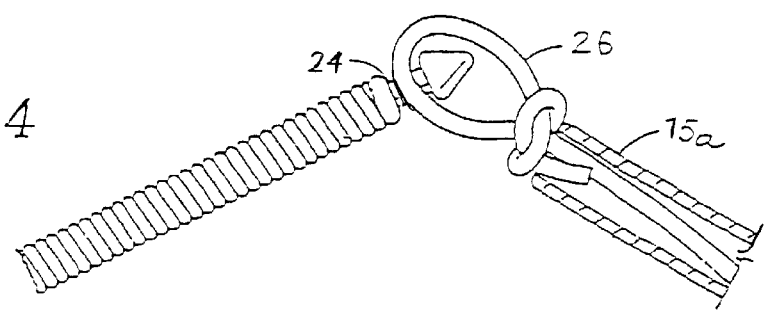
FIG. 4 is a fragmentary elevational view of one embodiment of a retrievable radiotherapy device of the present invention with a microsnare disposed in position to lasso the radiotherapy device for retrieval from the body.

The device 1 of the present invention may be used as a permanent implant, or alternatively, it can be adapted to permit retrieval and replacement if necessary or desired. In order to be retrieved, a device 1 may be provided with a head 24 (FIG. 4) having an enlarged shoulder, an angulated hook, or other suitable shaped surface on its distal or proximal end which may be lassoed by a microsnare device 26, which is known in the art, introduced through a microcatheter 15a. An example of one such arrangement is shown in FIG. 4. Fluoroscopic visualization may be used to assist in snaring the device 1. When lassoed or snared, the retrievable radiotherapy device 1 of the present invention can then be retrieved through the same microcatheter 15a. In the event the device 1 is intended as a permanent implant, its radioactivity must, of course, be properly selected, monitored, and controlled in order to avoid overexposure and possible damage to healthy tissues surrounding the implant site.

While preferred and alternative embodiments of the invention have been shown and described, many modifications thereof may be made by those skilled in the art without departing from the spirit of the invention. For example, radiotherapy devices of the present invention which are intended to be permanent implants in the vascular tree can be coated with a predetermined amount of bovine thrombin to produce the desired amount of thrombosis which can be useful in preventing potential bleeding from premature angionecrosis, or destruction of vessel tissue. Radiotherapy devices which are intended to be retrievable and replaceable and are implanted temporarily in the vascular tree can be coated with heparin, hirudin, or acetylsalicylic acid to prevent local thrombosis. Simultaneous systemic anticoagulation means are utilized to prevent a retrievable device of the present invention from producing thrombosis when implanted in the vascular tree. Both permanent and retrievable radiotherapy devices of the present invention can be modified to slowly release chemotherapeutic agents delivered selectively and in high concentration to the cancerous lesion. This will be particularly effective when delivering tumor-specific monoclonal antibodies in the case of cancer, or in the case of vascular malformations, by delivering sclerosing agents toxic to the endothelium or by delivering anti "angiogenesis factor" antibodies. Both permanent and retrievable radiotherapy devices of the present invention can be made of ferromagnetic material to act as ferromagnetic thermodevices to produce focal hyperthermia (i.e., local, focused heat) in addition to their thrombogenic and/or radiotherapeutic effects. Hyperthermia can be generated when the implanted ferromagnetic device is introduced into a high radio frequency field (e.g., of the order of 915 MHZ). In view of the many modifications and variations which are possible, the scope of the invention should be determined in accordance with the following claims.

I claim:

1. A radiotherapy device, comprising:
   a radioactive inner core, said inner core being adapted for permanent implantation in a selected body tissue site and for delivering a predetermined dosage of radiation to said body tissue site; and
   an outer layer disposed about said inner core and implantable with said inner core, said outer layer attenuating the radiation that is transmitted from said inner core to said body tissue site.

2. The radiotherapy device according to claim 1 wherein the outer layer comprises a coil.

3. The radiotherapy device according to claim 1 wherein the outer layer comprises a shape memory metal.

4. The radiotherapy device according to claim 1 wherein the inner core comprises a material selected from the group consisting of cobalt-60, cesium-137, iridium-192, iodine-125, palladium-103, tantalum-73, tungsten-74, and gold-198.

* * * * *